US010086147B2

(12) United States Patent
Despa et al.

(10) Patent No.: US 10,086,147 B2
(45) Date of Patent: Oct. 2, 2018

(54) DOSE CAPTURE DEVICE FOR SYRINGES

(71) Applicant: Becton, Dickinson and Company, Franklin Lakes, NJ (US)

(72) Inventors: Mircea Stefan Despa, Cary, NC (US); Andrew Richards, Durham, NC (US); Sundeep Kankanala, Chapel Hill, NC (US); Jonathan Hofius, San Francisco, CA (US); Thomas P. Low, Belmont, CA (US); Jose Luis Cordoba Matilla, Malaga (ES); Pablo Eduardo Garcia Kilroy, Menlo Park, CA (US); Karen Shakespear Koenig, San Francisco, CA (US); Joseph Eckerle, Woodside, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 185 days.

(21) Appl. No.: 15/004,792

(22) Filed: Jan. 22, 2016

(65) Prior Publication Data
US 2016/0213856 A1 Jul. 28, 2016

Related U.S. Application Data

(60) Provisional application No. 62/107,946, filed on Jan. 26, 2015.

(51) Int. Cl.
*A61M 5/315* (2006.01)
*A61M 5/31* (2006.01)

(52) U.S. Cl.
CPC ...... *A61M 5/31568* (2013.01); *A61M 5/3146* (2013.01); *A61M 2005/3126* (2013.01); *A61M 2005/3142* (2013.01); *A61M 2205/33* (2013.01); *A61M 2205/3576* (2013.01); *A61M 2205/50* (2013.01); *A61M 2205/52* (2013.01)

(58) Field of Classification Search
CPC ............ A61M 5/31568; A61M 5/3146; A61M 2005/3126; A61M 2205/3306; A61M 2205/50; A61M 2205/52; A61M 2205/3592; A61M 2205/18; A61M 5/16804; A61M 5/16886; A61M 5/1723; A61M 5/31525; G06F 19/3468; G06F 19/3462
USPC ... 604/65–67, 151, 111, 503, 506, 189, 152; 128/DIG. 12, DIG. 13
See application file for complete search history.

(56) References Cited

U.S. PATENT DOCUMENTS

| | | | |
|---|---|---|---|
| 2,117,469 A * | 5/1938 | Woodyatt | A61M 5/002 206/210 |
| 5,611,784 A | 3/1997 | Barresi et al. | |

(Continued)

FOREIGN PATENT DOCUMENTS

WO WO 2011/023628 A1 3/2011

OTHER PUBLICATIONS

International Search Report and Written Opinion in international application No. PCT/US16/14459, dated Apr. 21, 2016.

*Primary Examiner* — Manuel Mendez
(74) *Attorney, Agent, or Firm* — Knobbe Martens Olson & Bear, LLP (57) ABSTRACT

Described herein is a smart dose monitoring device. The dose monitoring device may include electronics such as motion sensors, orientation sensors, and timers related to monitoring the time of and amount of dose administered during an injection event.

23 Claims, 5 Drawing Sheets

(56) References Cited

U.S. PATENT DOCUMENTS

| | | | |
|---|---|---|---|
| 5,868,710 A * | 2/1999 | Battiato | A61M 5/14546 |
| | | | 128/DIG. 1 |
| 6,171,276 B1 * | 1/2001 | Lippe | A61M 5/20 |
| | | | 128/DIG. 1 |
| 7,195,616 B2 * | 3/2007 | Diller | A61M 5/31535 |
| | | | 604/207 |
| 9,250,111 B2 * | 2/2016 | Whalley | A61M 5/31 |
| 2004/0158205 A1 | 8/2004 | Savage | |
| 2005/0220639 A1 * | 10/2005 | Sasaki | A61M 5/1458 |
| | | | 417/415 |
| 2011/0009812 A1 | 1/2011 | Brown | |
| 2011/0257596 A1 | 10/2011 | Gaudet | |
| 2011/0313350 A1 | 12/2011 | Krulevitch | |
| 2015/0018775 A1 | 1/2015 | Groeschke | |

\* cited by examiner

DOSE CAPTURE DEVICE FOR SYRINGES

RELATED U.S. APPLICATIONS

This application claims priority to U.S. Provisional Appl. No. 62/107,946 filed on Jan. 26, 2015, which is hereby incorporated by reference in its entirety.

BACKGROUND OF THE INVENTION

Field of the Invention

The invention relates to syringes, and more particularly, relates to smart devices for capturing dosing data from syringes.

Description of the Related Art

There are multiple diseases wherein patients have an active role in disease management. Under some treatment regimens, a patient may be required to inject medicament into their body multiple times per day. For example, diabetic patients must self-inject insulin in order to control blood sugar levels. When preparing to self-inject medicament, a patient may need to take several factors into account. For example, a patient may need to keep track of previous injection dose amounts as well as the precise times at which those doses were administered in order to calculate the dose amount and time for a subsequent self-injection. Diabetic patients may need to inject insulin several times a day at varying levels. It can prove difficult for a patient to keep track of the dose amount and time of each injection event. Furthermore, after extracting insulin into a syringe, but before injection into a patient, some medicament may be lost from the syringe during "priming," the removal of air bubbles from the syringe. This may cause the patient to incorrectly remember the amount of insulin that was originally drawn into the syringe as the injected dose amount. These issues create a possibility of error in determining dose amounts and times which are used for subsequent self-injections.

In order to remedy these issues, the prior art has focused on sensors configured to monitor and track the linear distance traveled by a syringe stopper or plunger rod, which can be used to calculate the amount of fluid present in the syringe. However, a stopper or plunger rod can undergo several linear motions prior to injection of medicament. For example, to fill a syringe with insulin, a patient first fills the syringe with an amount of air equivalent to the amount of their intended insulin dose. The patient then pressurizes an insulin vial by injecting the air into the vial. With the syringe still in the vial, the patient then turns over the syringe and vial so that the needle end of the syringe is pointed upward. The patient then aspirates the insulin from the vial into the syringe. During this process, air may be drawn into the syringe along with the insulin. To remove the air, a patient may engage in priming, which involves several steps. First, a patient orients the needle end of the syringe straight upward. This rotation allows air to rise to the top of the needle. The patient may then tap on the syringe in order to dislodge bubbles from the sidewalls of the syringe. Next, the patient can depress the plunger until all of the air bubbles are emitted from the syringe. The multiple motions of the plunger prior to injection may all be recorded and lead to erroneous measurements of the distance traveled by the plunger during injection, and consequently of the dose amount.

SUMMARY OF THE INVENTION

One aspect of the invention is a dose monitoring device that can detect the motion of a plunger rod or stopper inside of a syringe and determine the orientation of the syringe when that motion occurs. The dose monitoring device can include a first channel configured to receive a syringe body of a syringe, one or more motion sensors configured to detect the movement of a plunger in the syringe body, one or more orientation sensors configured to detect the orientation of the syringe, one or more sensors configured to detect sudden motions of the syringe, a timer, and a communication module configured to transmit data from the one or more motion sensors, the one or more orientation sensors, the one or more sensors configured to detect sudden motions of the syringe, and the timer to an external device.

In one embodiment, the motion data and the orientation data can be transmitted to an external device.

Another embodiment of the present invention is a method for calculating and recording the dose amount and the precise time of previous medicament injections. The method may include providing a syringe having a plunger configured to administer a medicament, providing a dose monitoring device comprising one or more motion sensors, one or more orientation sensors, and a timer, wherein the dose monitoring device attaches to the syringe and is configured to detect data using the one or more motion sensors, the one or more orientation sensors, and the timer, transmitting the data to a processor, and determining which data corresponds to an injection event of the syringe.

DETAILED DESCRIPTION

As will be appreciated by one skilled in the art, there are numerous ways of carrying out the examples, improvements, and arrangements of a medicament delivery device in accordance with embodiments of the invention disclosed herein. Although reference will be made to the illustrative embodiments depicted in the drawings and the following description, these embodiments are not meant to be exhaustive of the various alternative designs and embodiments that are encompassed by the disclosed invention. Those skilled in the art will readily appreciate that various modifications may be made, and various combinations can be made, without departing from the invention.

One embodiment is a medicament dose monitoring device, as depicted in FIGS. 1-4. In an illustrative embodiment, the dose monitoring device is configured and shaped to mate with a typical syringe. In some embodiments, the dose monitoring device is configured and shaped so that it can be attached and detached from more than one type or shape of disposable syringe. For example, in one embodiment, the dose monitoring device is crescent shaped, and designed to mate with the upper portion of a syringe.

In an illustrative embodiment, the dose monitoring device can include one or more sensors for detecting data relevant to movement of the syringe by a user. For example, the movement may relate to an injection event, wherein the user is preparing for, or performing, an injection. The one or more sensors can include plunger motion sensors for detecting the linear motion of a plunger rod or stopper within a syringe. The plunger motion sensors can be configured to detect the distance and direction traveled by the plunger rod or stopper. In one embodiment the plunger fits within a recess within the dose monitoring device. The recess includes a motion sensor that detects the linear movement of the plunger.

The dose monitoring device can also include one or more orientation sensors for determining the orientation of the syringe and for detecting sudden motions associated with syringe handling. The orientation sensors can be configured to detect motions of the syringe such as, but not limited to, sudden impacts associated with tapping on the side of the syringe. In some embodiments, different orientation sensors are configured to determine orientation of the syringe than are configured to determine motions associated with syringe handling. In an illustrative embodiment according to the present invention, the dose monitoring device can further include a digital clock or timer to record the time associated with the motion of the plunger rod or stopper of the syringe.

In an illustrative embodiment according to the present invention, the dose monitoring device may further include a communication module to allow for connectivity between the dose monitoring device and external devices. The communication module can be connected to an external device using wired or wireless communication. This connection may be made using well-known wireless communication protocols, such as Bluetooth, WIFI, or other means. The dose monitoring device may further include a battery to provide power to the electrical components of the dose monitoring device.

The dose monitoring device may also be configured to transmit data from the sensors to an external device, such as a computer or mobile device. The external device may be configured to process the data to determine which motions of the plunger or stopper are associated with an injection event. Data for the distance traveled by the plunger during an injection event can then be processed to calculate the amount of medicament expelled from the syringe, i.e., the amount of dose injected into a user. The amount of dose and the time associated with an injection event can then be recorded and displayed to a user on a user interface of the external device.

A user may attach the dose monitoring device to a syringe prior to performing an injection. For example, a diabetic patient may attach the dose monitoring device to an empty syringe in advance of performing an insulin injection. In this example, the user would either power up the device, or the device would automatically power up upon being mated with a syringe. The device would then detect the lateral movement of the syringe as the user draws the plunger outwards from the syringe body into order to fill the syringe with the proper amount of air prior to pressurizing an insulin vial. The device may detect that the syringe was moved outwardly corresponding to one unit of insulin, based on the type of syringe designed to mate with the device. The device may then detect the user pressing the plunger downward to pressurize the insulin vial.

During these operations, an orientation sensor may be actively recording the orientation of the syringe for later analysis. This allows the system to process and more accurately predict determine when the actual doing occurred based on the prior, and current, position of the syringe in three-dimensional space. For example, it's unlikely that movement of the plunger downward while the needle is facing up would be an injection event. Normally, an injection event would occur with the needle either facing downwards or approximately parallel with the ground.

Once the user has pressurized the insulin vial, the system may detect the user orienting the needle upwards and withdrawing a particular amount of insulin from the pressurized vial. Detection of the needle in the upwards position, and a withdrawal movement of the plunger may signal this event to the dose monitoring device. The system may then store the amount of calculated insulin based on how far the plunger was withdrawn during this event.

The dose monitoring device may then monitor movement of the syringe to determine if the user performing a priming operation. In such an operation, the user may "flick" or knock the syringe in order to release trapped air bubbles. This is normally performed with the needle facing upwards so that any trapped air bubbles move to the top of the syringe. The user may then slightly depress the plunger to expel any trapped air. During this process of expelling the air, the use may also release some of the medicament, in this case insulin, from the syringe. This would reduce the amount of insulin actually injected, and so the device may track the plunger movement during this event, so the later calculation of how much insulin was injected would be more accurate.

Following priming, the device would monitor for an event wherein the needle is facing downward, or mostly parallel with the ground, and the plunger is depressed all the way back in to the needle body. This would signal an injection event. From the movement of the plunger, and the prior stored data relating to the movement of the plunger during the earlier phases, the device can accurately predict and store the amount of insulin, or any medicament, administered to the user.

It should be realized that the dose monitoring device may be configurable so that different capacity syringes may be mated with the device and the device would properly calculate the amount of medicament being injected. Thus, the device will recognize a syringe type automatically, or the user may select a particular size syringe by, for example, selecting particular buttons on the device, or alternatively by linking the device through a port to a computer system.

Although various persons, including, but not limited to, a patient or a healthcare professional, can operate or use illustrative embodiments of the present invention, for brevity an operator, patient or user will be referred to as a "user" hereinafter.

Although various fluids can be employed in illustrative embodiments of the present invention, fluid in a syringe will be referred to as "medicament" hereinafter.

Figure 1:
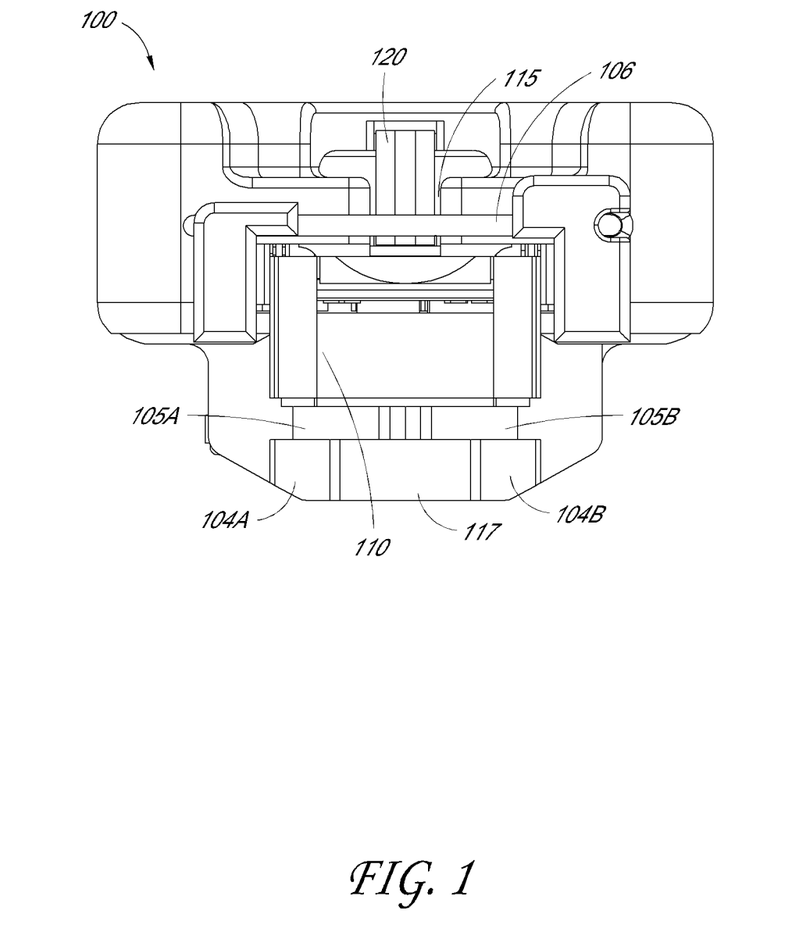
FIG. 1 depicts a dose monitoring device for a syringe in accordance with an illustrative embodiment of the present invention.

FIG. 1 depicts an illustrative embodiment of a crescent-shaped dose monitoring device 100. A lower portion of the dose monitoring device 100 includes a barrel channel 117 that is configured to mate with a barrel of a syringe. The barrel channel 117 has a set of protrusions 104A,B that define the outer periphery of the barrel channel 117 and help hold the barrel to a syringe.

Above the barrel channel 117 is a set of flange coupling slots 105A,B that are configured to mate with a syringe flange. A syringe flange, when mounted, would rest above the protrusions 104A,B and slidably engage with the coupling slots 105A,B so that the syringe does not move with respect to the device 100 when they are mated together. Although this embodiment illustrates slots for engaging with the syringe, it should be realized that other coupling mechanisms, such as fasteners, clips or other engagement means are also contemplated.

Positioned above the coupling slots 105A,B in the device 100 is a rectangular recess 110 that is configured to mate with an upper portion of a syringe. Above the rectangular recess 110 is a plunger rod channel 115 configured to mate with a syringe plunger. Within the plunger rod channel 115 is a motion sensor 120 that is configure to measure the movement of a plunger rod on a mounted needle. Across from the channel 115 is a retaining rod 106 configured to help hold the plunger rod in place.

The dose monitoring device 100 may further comprise a connection port (not shown) such as a USB port.

Figure 2:
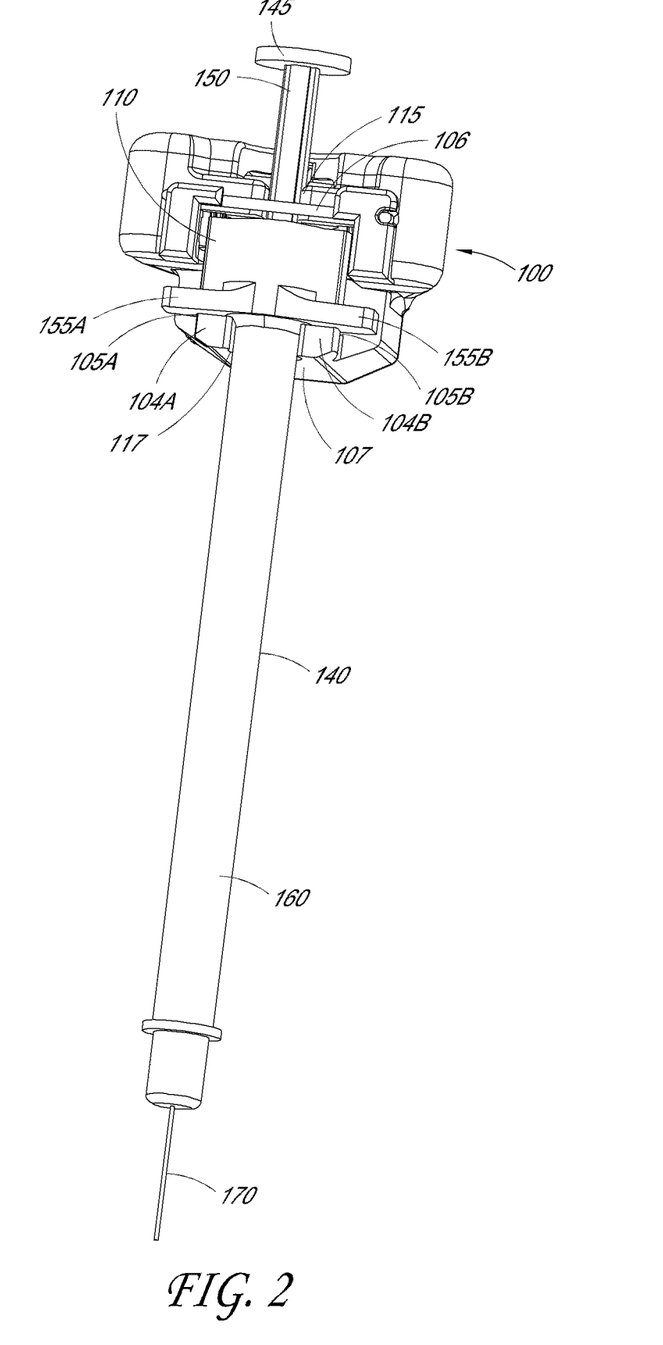
FIG. 2 depicts a dose monitoring device coupled to a syringe in accordance with an illustrative embodiment of the present invention.

FIG. 2 depicts an illustrative embodiment of the dose monitoring device 100 coupled to a syringe 140. The syringe 140 comprises a plunger 145, a plunger rod 150, a set of flanges 155A,B, a barrel 160, a needle 170, and a stopper (not shown). The stopper is attached to the end of the plunger rod 150 located in the interior of the barrel 160. In an illustrative embodiment, the syringe 140 is an insulin syringe. The needle 170 can be, but is not limited to a 6 mm, 8 mm, or 12.7 mm length needle. The needle 170 can also be, but is not limited to, a 28 gauge, 30 gauge, or 31 gauge needle.

FIG. 2 also shows how the set of flange coupling slots 105A,B, the rectangular recess 110, and the plunger rod channel 115 of the dose monitoring device 100 engage the syringe 140. The set of flanges 155A,B engage the set of flange coupling slots 105A,B. The barrel 160 engages the barrel channel 117. The plunger rod is located within the plunger opening 115. The plunger end of the syringe engages with the rectangular recess 110. A lip 107 of the dose monitoring device 100 can be configured to allow a user to grip the device and engage the plunger with one hand.

In operation, the plunger 145 can be displaced linearly into or out of the interior of the barrel 160. When the plunger 145 is displaced linearly out of the barrel 160, fluid is drawn in through the needle 170 and into the barrel 160. When the plunger 145 is displaced into the barrel 160, fluid is emitted out of the barrel 160 through the needle 170. The stopper creates a seal along the sidewalls of the barrel so that fluid is confined to the section of the barrel between the stopper and the needle.

The plunger 145 may be displaced several times during the preparation and injection of medicament. The dose monitoring device 100 may be configured to detect and measure the linear distance and direction of travel of the plunger during each displacement using the motion sensor 120. An integrated accelerometer may be used to determine the orientation of the syringe 140 during each displacement. In addition, the time of each displacement may be measure and recorded with an internal timer. The linear distance and direction data, orientation data, and time data can be stored in a memory and transmitted to an external device by a communication module, as discussed more fully with reference to FIG. 3 below.

The set of flange coupling slots 105A,B are configured and shaped so that the flange of a syringe can be mounted inside of the coupling slots 105A,B. The rectangular recess 110 is configured and shaped so that the dose monitoring device can be mounted to the plunger end of a syringe. The plunger rod channel 115 is configured to allow for the linear motion of a plunger rod both into and out of the syringe. In one embodiment, motion sensors are located in the rod channel 115.

Figure 3:
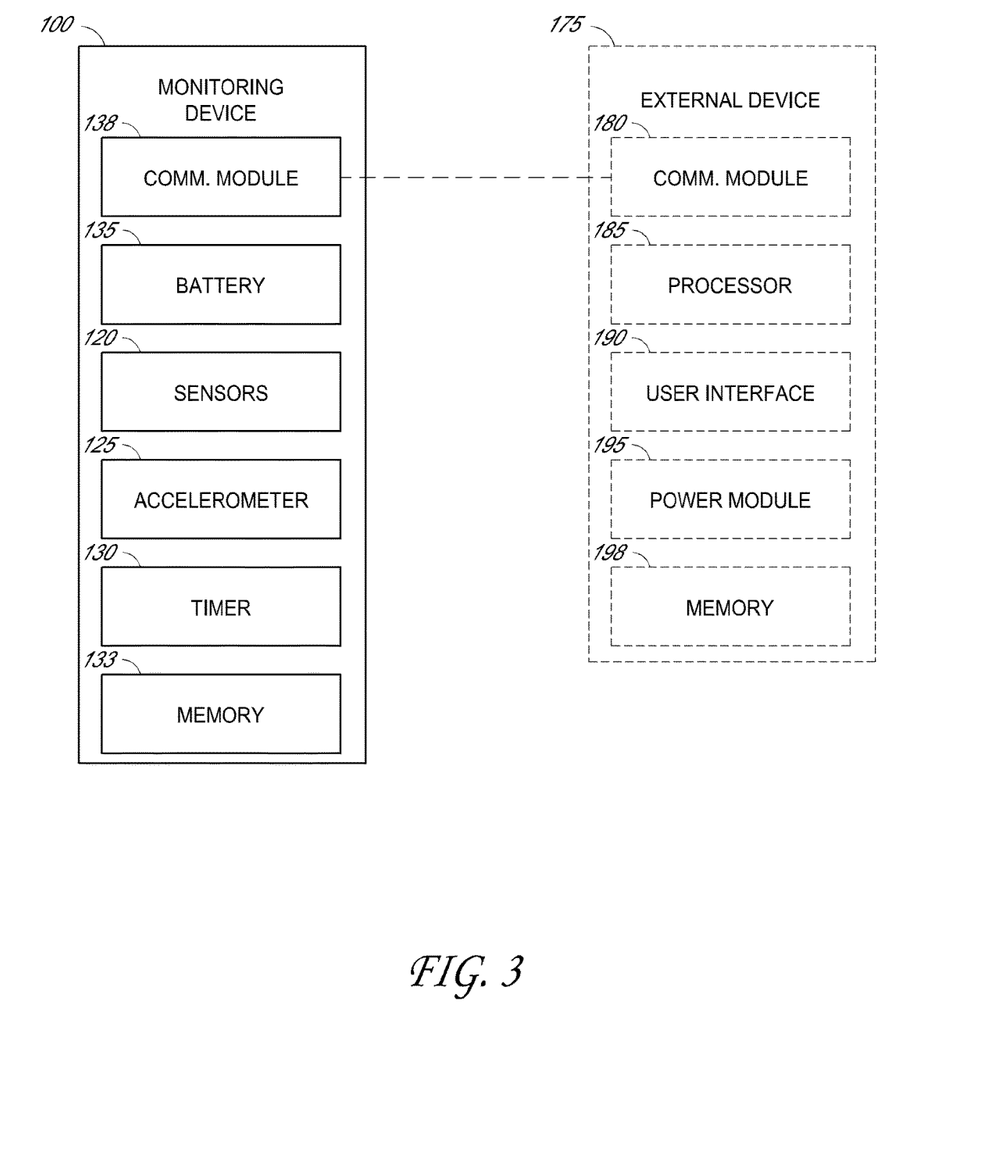
FIG. 3 depicts a schematic view of a dose monitoring device in accordance with an illustrative embodiment of the present invention.

FIG. 3 depicts a schematic view of an illustrative embodiment of a dose monitoring device 100. The dose monitoring device 100 comprises a communication module 138, a battery 135, the motion sensors 120, an accelerometer 125, a timer 130 and a memory 133. In an illustrative embodiment, the communication module 138 can communicate with an external device 175 such as a mobile device, computer, server, or any other electronic external device that is known in the art. The external device 175 can include a communication module 180 for receiving data from the communication module 138. The external device 175 may also include a user interface 190 for accessing and reading data on the external device. The external device may further comprise a processor 185. The processor 185 can be configured to perform on-board processing of data received from the smart dosage device 100 using algorithms to determine the precise time that an injection occurred and the amount of dose administered. The external device 175 may further include a power module 195 to provide power to the electrical components of the external device.

The motion sensors 120 can be configured to detect and measure the linear distance and direction of travel of a plunger rod or stopper of a syringe using one or more of magnetic, resistive, capacitive, optical, and mechanical sensing. In one embodiment, the motion sensors 120 may comprise an encoder mechanism. The encoder mechanism can be a rotary-to-linear mechanism including an encoder wheel that engages a plunger rod of a syringe so that linear movement of the plunger rod causes the wheel to rotate. The encoder mechanism can measure the rotation of the wheel as the plunger rod moves in order to detect and calculate the linear distance and direction of travel of the plunger rod. The motion sensors 120 may further comprise an optical system including one or more light sources and one or more light detectors that can detect and measure the linear motion of the plunger rod or stopper.

The accelerometer 125 can be configured to determine the orientation of the dose monitoring device 100. Consequently, the accelerometer 125 can be used to determine the orientation of a syringe when the dose monitoring device 100 is coupled to the syringe. The accelerometer 125 can be further configured to detect sudden motions of the syringe, such as, for example, those that may occur when a user taps on the syringe during priming. The accelerometer 125 may comprise a single-axis accelerometer or a multiple-axis accelerometer. It should be recognized the accelerometer 125 is not limited to an accelerometer, but may include any orientation sensor known in the art.

The timer 130 can be configured to record a time at each instance that the motion sensors 120 and accelerometer 125 obtain data so that each set of data has an associated time. The time 130 can measure the amount of time that the dose monitoring device 100 is in a particular orientation. The motion sensors 120 and accelerometer 125 can be configured to obtain data at defined time intervals. Alternatively, the motions sensors 120 and accelerometer 125 can be configured to obtain data every time the plunger rod or stopper experience linear motion. In one embodiment, the timer 130 can comprise a digital clock.

The battery 135 can be configured to supply power to the electrical components of the dose monitoring device 100. The battery 135 may be rechargeable. The battery 135 may also include an external switch. In one embodiment, the dose monitoring device 100 can be configured so that the motion sensors 120, the accelerometer 125, and the timer 130 are activated at any time that the battery 135 is supplying power to the dose monitoring device 100. In an alternative embodiment, the motion sensors 120, the accelerometer 125, and the timer 130 can be activated when the dose monitoring device 100 is coupled to a syringe.

The memory 133 can be configured to store data from the motion sensors 120, the accelerometer 125, and the timer 130.

The communication module 138 can be configured to allow the transmission of data to an external device. The communication module 138 can be connected to an external device through a wired or wireless connection. The communication module 138 can be configured to perform short-distance RF communication, such as Bluetooth, BLE, or ZigBee®. The dose monitoring device 100 can further comprise one or more ports or slots to allow for a wired connection between the dose monitoring device 100 and an external device. Furthermore, the dose monitoring device 100 may comprise a data storage device such as a flash drive or memory card, or may be configured to engage such a data storage device in order to transmit data to an external device.

The battery 135 can be configured to supply power to the electrical components of the dose monitoring device 100.

As described above, the motion sensors 120 can detect and measure the linear distance and direction of travel of a plunger of a syringe. The accelerometer 125 can detect angular position of a syringe as well as sudden movement events associated with the syringe. In an illustrative embodiment, the processor 185 can be configured to process the data streams supplied by the motion sensors 120, the accelerometer 125, and the timer 130 to determine which portion of the linear movement of the plunger is associated with an injection event, at what time the injection event occurred, and the time over which the injection event occurred. For example, the processor 185 can be configured to run a process that rejects data when it is detected that a plunger is withdrawn from a barrel of a syringe irrespective of the detected orientation of the syringe because such withdrawal would not constitute an injection event.

The processor 185 may further be configured to reject data recorded when it is detected that the plunger is advancing into the barrel of the syringe, but the detected orientation of the syringe is such that the needle is pointed upwards above a certain angle. Furthermore, the processor may be configured to reject data recorded when it is detected that a plunger is advancing into the barrel of the syringe, but a sudden motion is detected to have occurred after the movement of the plunger, such as tapping of the syringe as may occur during priming. In contrast, the processor 185 can be configured to accept sensor data if it is detected in the most recent motion of the plunger that the plunger was advancing into the barrel of the syringe, that the orientation of the syringe was generally so that the needle was pointed downward below a certain angle, and that there were no sudden syringe motions associated with the travel of the plunger. These conditions are likely to be present in the event of an actual injection. However, the processor 185 may be configured to reject such data if it is determined that a linear movement out of the plunger occurred shortly after the linear movement into the plunger, and the linear movement out of the plunger occurred when the syringe was oriented in an upward direction. This may be indicative of pressurization rather than injection. The processor 185 can further be configured to perform calculations using the distance traveled by the plunger during injection to determine the amount of dose expelled from the syringe during injection.

The calculated amount of dose and the time data associated with the injection event can be recorded to the memory 198 and displayed on a user interface 190.

It should be recognized that a user may connect the dose monitoring device 100 to the external device 175 after multiple dose administrations. The processer 185 can be configured to accept data for more than one recorded motion of a plunger during each connection to the dose monitoring device 100.

The user interface 190 can be configured to allow a user to access the amount of dose data and time data recorded in the memory 198. A user may access this data to determine an amount of dose and time for their next injection. The user interface may comprise a touch screen, a keyboard and display screen, or any other user interface known in the art.

In one embodiment, the memory 198 is configured to retain data for a defined number of the most recent injections. In an alternative embodiment, the memory 198 may be configured to retain data for only the most recent recorded injection.

Figure 4:
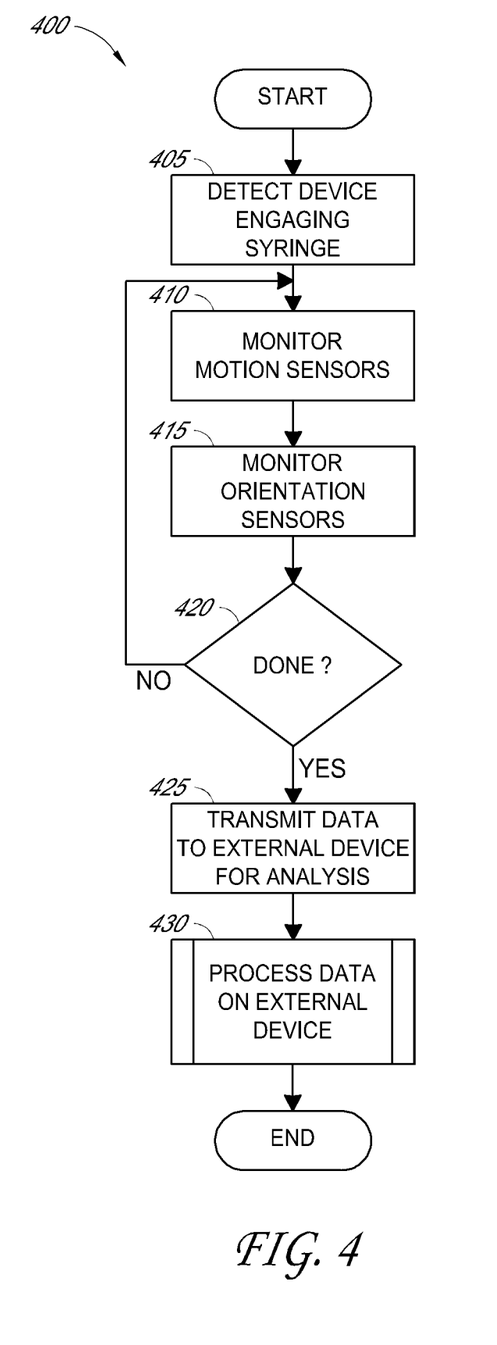
FIG. 4 depicts a flowchart of an embodiment of monitoring an injection event in accordance with an illustrative embodiment of the present invention.

FIG. 4 depicts a flowchart of a process 400 for an embodiment of monitoring an injection event in accordance with an illustrative embodiment of the present invention. The process 400 begins at a start step and then moves to a step 405, wherein a dose monitoring device, such as dose monitoring device 100 depicted in FIGS. 1-3, is engaged to a syringe, such as syringe 140 depicted in FIG. 2. After the dose monitoring device is engaged to the syringe, the process 400 moves to a step 410, wherein data starts to be monitored by one or more motion sensors, such as motion sensors 120 depicted in FIGS. 1-3. The motion sensors may detect distance traveled and direction traveled by a plunger rod of a syringe.

After data starts to be monitored by the motion sensors, the process 400 moves to a step 415, wherein data starts to be monitored by one or more orientation sensors, such as accelerometer 125 depicted in FIGS. 1-3. The orientation sensors may detect the angle at which a needle of the syringe is oriented or if sudden movements of the syringe have occurred. After data starts to be monitored by the orientation sensors, the process 400 moves to a decision step 420, wherein a decision is made whether data from the motion sensors and orientation sensors is done being monitored. The data may be done being monitored when it is detected that the dose monitoring device is disengaged from the syringe. Alternatively, the data may be done being monitored when the dose monitoring device is connected to an external device, such as external device 175 depicted in FIG. 3.

If a decision is made at the decision step 420 that the data is not done being monitored, the process 400 returns to the step 410. If a decision is made at the decision step 420 that the data is done being monitored, then the process 400 moves to a step 425, wherein data is transmitted from the dose monitoring device to an external device for analysis. This may be performed by a communication module, such as communication module 138 depicted in FIG. 3.

After the data is transmitted to an external device, the process 400 moves to a process step 430, wherein the data is processed on the external device. The functions of process step 430 will be explained further in reference to FIG. 5. After the data is processed on the external device, the process 400 concludes at an end step.

Figure 5:
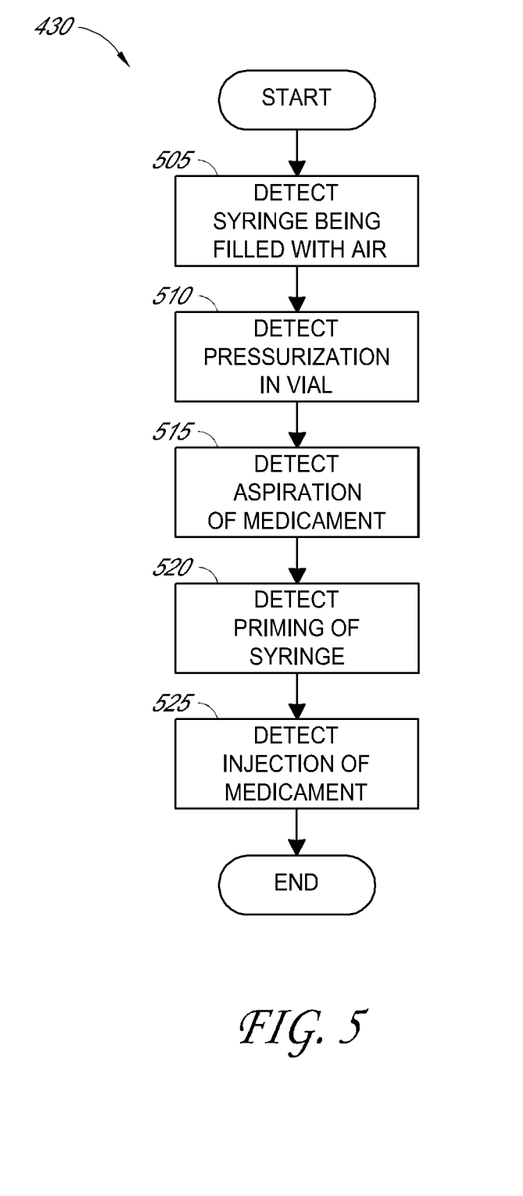
FIG. 5 depicts a flowchart of an embodiment of processing sensor data on an external device in accordance with an illustrative embodiment of the present invention.

FIG. 5 depicts a flowchart of a process 430 of an illustrative embodiment of processing data on an external device. The process 430 begins at a start step, and then moves to a step 505, wherein the device detects that a set of data corresponds to the syringe being filled with air. This detection can be made my monitoring the linear motion data of the syringe and noting that a distance traveled by a plunger, such as plunger 145 depicted in FIG. 2 was in a direction out of a barrel of the syringe, such as barrel 160 depicted in FIG. 2. This type of data may occur when an amount of air equivalent to the amount of medicament intended to be injected is aspirated into the syringe. For example, the data from the motion sensors may note that the plunger, such as plunger 145 depicted in FIG. 2, is withdrawn from a barrel of the syringe, such as barrel 160 depicted in FIG. 2.

In addition, the orientation data can be monitored, and the device can note when the position of the syringe was in an upward orientation. This is a typical orientation wherein air is withdrawn during this step. Further, the time that the data was recorded can be monitored and it may be noted that there were no linear motions of the plunger shortly preceding the linear motion of the plunger out of the barrel. The time data can be used to differentiate between filling with air and aspirating medicament. After the device detects that a set of data corresponds to the syringe being filled with air, the process 430 moves to a step 510, wherein the device detects that a set of data corresponds to pressurizing a vial of medicament using the syringe. This detection can be made by monitoring the linear motion data of the syringe and noting that a distance was traveled by the plunger in a direction into the barrel of the syringe. In addition, the orientation data can be monitored to detect that the position of the syringe was in a downward orientation. This is a typical orientation wherein a vial of medicament is pressurized. Furthermore, the time of the movement of the plunger can be monitored and compared to the time of other linear movements to distinguish from other movements of the syringe. For example, if the time of the linear movement is closely followed by a linear movement that is found to indicate aspiration of medicament, which will be explained below, it may be determined that the linear motion of the plunger into the barrel constituted pressurization of a vial and not an injection event.

After the device detects that a set of data corresponds to pressurizing a vial of medicament using the syringe, the process 430 moves to a step 515, wherein the device detects that a set of data corresponds to the aspiration of medicament into a syringe. This detection can be made by monitoring the linear motion data of the syringe and noting that a distance was traveled by the plunger in a direction out of the barrel of the syringe. In addition, the orientation data can be monitored to detect that the position of the syringe was in an upward orientation. This is a typical orientation wherein a vial of medicament is aspirated. Furthermore, the time that the data was recorded can be monitored and it may be noted that there were linear motions of the plunger into the barrel shortly preceding the linear motion of the plunger out of the barrel. The time data can be used to differentiate between filling with air and aspirating medicament.

After the device detects that a set of data corresponds to the aspiration of medicament, the process 430 moves to a step 520, wherein the device detects that a set of data corresponds to the priming of a syringe. This detection can be made by monitoring the orientation sensor data and noting sudden movements of the syringe. Sudden movements are typical when a syringe is primed to remove air bubbles.

After the device detects that a set of data corresponds to priming of the syringe, the process 430 moves to a step 525, wherein the device detects that a set of data corresponds to the injection of medicament into a patient. This detection can be made by monitoring the linear motion data of the syringe and noting that a distance was traveled by the plunger in a direction into the barrel of the syringe. In addition, the orientation data can be monitored to detect that the position of the syringe was in a downward orientation. This is a typical orientation wherein medicament is injected. In addition, the time of the data can be monitored and it can be noted that there was no travel of the plunger in a distance out of the barrel closely following the movement of the plunger into the barrel.

After the device detects that a set of data corresponds to the injection of medicament into a patient, the process 430 concludes at an end step.

In an illustrative embodiment, the data for the syringe functions detected by the process 400 can be recorded in a memory of the external device, such as memory 198 depicted in FIG. 3. The distance traveled data for each syringe function may further be processed to determine the volume of fluid present in the barrel during each syringe function. Data for the syringe functions detected by the process 400 can also be displayed on a user interface, such as user interface 190 depicted in FIG. 3.

Implementations disclosed herein provide systems, methods and apparatus for a module configured to mate with an injector device. One skilled in the art will recognize that these embodiments may be implemented in hardware, software, firmware, or any combination thereof The functions described herein may be stored as one or more instructions on a processor-readable or computer-readable medium. The term "computer-readable medium" refers to any available medium that can be accessed by a computer or processor. By way of example, and not limitation, such a medium may comprise RAM, ROM, EEPROM, flash memory, CD-ROM or other optical disk storage, magnetic disk storage or other magnetic storage devices, or any other medium that can be used to store desired program code in the form of instructions or data structures and that can be accessed by a computer. Disk and disc, as used herein, includes compact disc (CD), laser disc, optical disc, digital versatile disc (DVD), floppy disk and Blu-ray® disc where disks usually reproduce data magnetically, while discs reproduce data optically with lasers. It should be noted that a computer-readable medium may be tangible and non-transitory. The term "computer-program product" refers to a computing device or processor in combination with code or instructions (e.g., a "program") that may be executed, processed or computed by the computing device or processor. As used herein, the term "code" may refer to software, instructions, code or data that is/are executable by a computing device or processor.

Software or instructions may also be transmitted over a transmission medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component or directly connected to the second component. As used herein, the term "plurality" denotes two or more. For example, a plurality of components indicates two or more components.

The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

In the foregoing description, specific details are given to provide a thorough understanding of the examples. However, it will be understood by one of ordinary skill in the art that the examples may be practiced without these specific details. For example, electrical components/devices may be shown in block diagrams in order not to obscure the examples in unnecessary detail. In other instances, such components, other structures and techniques may be shown in detail to further explain the examples.

Headings are included herein for reference and to aid in locating various sections. These headings are not intended to limit the scope of the concepts described with respect thereto. Such concepts may have applicability throughout the entire specification.

It is also noted that the examples may be described as a process, which is depicted as a flowchart, a flow diagram, a finite state diagram, a structure diagram, or a block diagram. Although a flowchart may describe the operations as a sequential process, many of the operations can be performed in parallel, or concurrently, and the process can be repeated. In addition, the order of the operations may be re-arranged. A process is terminated when its operations are completed. A process may correspond to a method, a function, a procedure, a subroutine, a subprogram, etc. When a process corresponds to a software function, its termination corresponds to a return of the function to the calling function or the main function.

The previous description of the disclosed implementations is provided to enable any person skilled in the art to make or use the present invention. Various modifications to these implementations will be readily apparent to those skilled in the art, and the generic principles defined herein may be applied to other implementations without departing from the spirit or scope of the invention. Thus, the present invention is not intended to be limited to the implementations shown herein but is to be accorded the widest scope consistent with the principles and novel features disclosed herein.

What is claimed is:

1. A dose monitoring device configured to mate with a syringe having a plunger that is slidably engaged in a barrel of the syringe, comprising:
    a first channel configured to receive a syringe body of the syringe;
    one or more motion sensors in contact with a rod of the plunger and configured to detect movement of the plunger into or out of the barrel of the syringe body;
    one or more orientation sensors configured to detect upward and downward orientations of the syringe; and
    a communication module configured to transmit data to an external device from the one or more motion sensors and the one or more orientation sensors.

2. The device of claim 1, wherein the one or more motion sensors comprise a rotary-to-linear encoder.

3. The device of claim 1, wherein the one or more orientation sensors comprise one or more accelerometers.

4. The device of claim 1, wherein the one or more orientation sensors are configured to detect sudden motions of the syringe.

5. The device of claim 1, further comprising a rod channel configured to engage a rod of the plunger of the syringe.

6. The device of claim 5, wherein the one or more orientation sensors are mounted within the rod channel.

7. The device of claim 1, further comprising a timer configured to measure the time the device is in a particular orientation.

8. The device of claim 7, wherein the communication module is configured to transmit data wirelessly to the external device.

9. The device of claim 1, further comprising one or more slots configured to receive one or more flanges of the syringe.

10. The device of claim 1, further comprising a memory configured to store data from the one or more motion sensors and the one or more orientation sensors.

11. The dose monitoring device of claim 1, further comprising a second channel configured to receive the rod of the plunger of the syringe, wherein the one or more motion sensors are mounted in the second channel.

12. The dose monitoring device of claim 11, wherein the one or more motion sensors are configured to measure the linear distance of travel of the rod of the plunger.

13. The dose monitoring device of claim 1, wherein the one or more motion sensors contact the rod of the plunger through one or more of magnetic, resistive, capacitive, optical, or mechanical sensing.

14. A method for recording the injection time and the amount of liquid injected by a syringe, comprising:
    providing a syringe having a plunger that is slidably engaged in a barrel of the syringe, wherein the syringe is configured to administer a medicament;
    providing a dose monitoring device comprising one or more plunger sensors and one or more orientation sensors;
    detecting a movement event by monitoring the orientation sensor to detect upward and downward orientations of the syringe;
    detecting an injection event by monitoring the plunger sensor to detect movement of the plunger into or out of the barrel of the syringe; and
    transmitting data from the one or more plunger sensors and the one or more orientation sensors based on the detected movement event or injection event to an external device.

15. The method of claim 14, wherein the one or more plunger sensors are configured to detect a direction and a distance traveled by the plunger of the syringe.

16. The method of claim 14, wherein the one or more orientation sensors are configured to detect an angle of orientation of the syringe.

17. The method of claim 14, wherein the one or more orientation sensors are configured to detect sudden movement of the syringe.

18. The method of claim 14, wherein the one or more motion sensors comprise a rotary-to-linear encoder.

19. The method of claim 14, wherein the one or more orientation sensors comprise an accelerometer.

20. The method of claim 14, wherein the syringe is an insulin syringe.

21. The method of claim 14, further comprising displaying an amount of previous injection on a user interface.

22. The method of claim 14, further comprising measuring the time of the detected injection event and displaying a time of previous injection on a user interface.

23. The method of claim 14, further comprising determining a priming event of the syringe prior to determining the injection event.

\* \* \* \* \*